United States Patent
Irani et al.

(10) Patent No.: US 10,041,348 B2
(45) Date of Patent: Aug. 7, 2018

(54) OPTICAL DEVICE AND METHOD FOR PREDICTING AND MITIGATING HYDRATE FORMATION USING AN INTEGRATED COMPUTATION

(71) Applicant: Halliburton Energy Services, Inc., Houston, TX (US)

(72) Inventors: Cyrus Irani, Houston, TX (US); Hendrik Kool, Conroe, TX (US)

(73) Assignee: Halliburton Energy Services, Inc., Houston, TX (US)

(*) Notice: Subject to any disclaimer, the term of this patent is extended or adjusted under 35 U.S.C. 154(b) by 496 days.

(21) Appl. No.: 14/438,561

(22) PCT Filed: Dec. 27, 2012

(86) PCT No.: PCT/US2012/071745
§ 371 (c)(1),
(2) Date: Apr. 24, 2015

(87) PCT Pub. No.: WO2014/105015
PCT Pub. Date: Jul. 3, 2014

(65) Prior Publication Data
US 2015/0285071 A1 Oct. 8, 2015

(51) Int. Cl.
*E21B 49/08* (2006.01)
*G01N 33/28* (2006.01)
(Continued)

(52) U.S. Cl.
CPC ............ *E21B 49/08* (2013.01); *E21B 47/102* (2013.01); *G01N 33/2823* (2013.01); *G01V 3/18* (2013.01); *G01V 8/20* (2013.01); *E21B 2049/085* (2013.01)

(58) Field of Classification Search
CPC .... G01N 21/31; G01N 21/3577; G01N 21/85; E21B 49/08; E21B 49/00; E21B 47/00
(Continued)

(56) References Cited

U.S. PATENT DOCUMENTS

| 5,166,747 A | 11/1992 | Schroeder et al. |
| 2002/0166818 A1* | 11/2002 | Henriot .................... B01J 49/05 210/670 |

(Continued)

FOREIGN PATENT DOCUMENTS

WO   WO 2014/093629 A1   6/2014

OTHER PUBLICATIONS

Supplementary European Search Report issued for EP 12890931 dated Oct. 4, 2016.
(Continued)

*Primary Examiner* — Roy Y Yi
*Assistant Examiner* — Jeffrey Aiello
(74) *Attorney, Agent, or Firm* — Haynes and Boone, LLP

(57) ABSTRACT

An optical computing device and method utilizing an Integrated Computational Element ("ICE") to predict and/or mitigate hydrate formation. Fluid is allowed to flow through a first conduit. A sample fluid is separated from the fluid flowing through the first conduit. The sample fluid is allowed to flow through a second conduit. At least one property of the sample fluid corresponding to hydrate formation is detected using at least one Integrated Computational Element ("ICE") computing device positioned along a tubular. A determination is made as to whether the detected at least one property is adequate for hydrate formation.

20 Claims, 3 Drawing Sheets

(51) Int. Cl.
  *G01V 3/18* (2006.01)
  *G01V 8/20* (2006.01)
  *E21B 47/10* (2012.01)

(58) Field of Classification Search
  USPC .......................................... 702/6, 11, 12, 25
  See application file for complete search history.

(56) References Cited

U.S. PATENT DOCUMENTS

| | | |
|---|---|---|
| 2003/0056581 A1 | 3/2003 | Turner et al. |
| 2008/0066908 A1* | 3/2008 | Oddie ................... E21B 49/08 166/264 |
| 2009/0078860 A1 | 3/2009 | Kischkat et al. |
| 2010/0108314 A1 | 5/2010 | Oddie |
| 2011/0024361 A1* | 2/2011 | Schwartzel ............ C02F 1/325 210/143 |
| 2012/0013335 A1 | 1/2012 | Saasen et al. |
| 2014/0056108 A1* | 2/2014 | Chelminski ............ G01V 1/135 367/143 |
| 2014/0110105 A1* | 4/2014 | Jones ..................... E21B 47/10 166/250.01 |
| 2014/0116120 A1* | 5/2014 | Seckar ................... G01N 21/03 73/64.56 |

OTHER PUBLICATIONS

International Search Report and The Written Opinion of the International Searching Authority, or the Declaration, dated Sep. 25, 2013, PCT/US2012/071745B1, 16 pages, ISA/KR.

\* cited by examiner

OPTICAL DEVICE AND METHOD FOR PREDICTING AND MITIGATING HYDRATE FORMATION USING AN INTEGRATED COMPUTATION

The present application is a U.S. National Stage patent application of International Patent Application No. PCT/US2012/071745, filed on Dec. 27, 2012, the benefit of which is claimed and the disclosure of which is incorporated herein by reference in its entirety.

FIELD OF THE INVENTION

The present invention relates generally to optical systems and, more specifically, to an optical computing device that utilizes an Integrated Computational Element ("ICE") to predict and mitigate the formation of hydrates in hydrocarbon environments.

BACKGROUND

Gas hydrates are crystallized water-based solids which naturally occur in a variety of environments, such as the vicinity of hydrocarbon formations. One such example is methane gas, which exists in subsea formations as methane hydrate, a crystallized methane deposit primarily located in vast amounts at shallow depths beneath the ocean floor. Hydrate formation requires a specific set of components and conditions: light hydrocarbons in the C1 to C3 range, water, low temperature, and high pressure. If the conditions are right, the water phase can interact with the gas to form a clatharate structure which is almost ice like in consistency.

However, hydrates can prove quite problematic during offshore drilling, exploratory, and production operations. For example, hydrate formation can lead to significant blockage of crucial flow paths with all the attendant safety and productivity issues. This is especially relevant in sub-sea systems such as, for example, a sub-sea safety tree which tends to be located right at the sea bed where conditions are ideal for hydrate formation. In addition, during downhole operations, methane hydrates may undergo sublimation, whereby the methane is released as gas out into the atmosphere. Therefore, some method by which hydrate formation could be predicted would be quite useful to the industry.

Accordingly, there is a need in the art for a minimally invasive optical computing device utilizing ICE structures that allows for constant monitoring of the environment, especially the gas composition, so that a real time understanding of the potential for hydrate formation is available, and appropriate mitigation efforts might be undertaken.

DESCRIPTION OF ILLUSTRATIVE EMBODIMENTS

Figure 1:
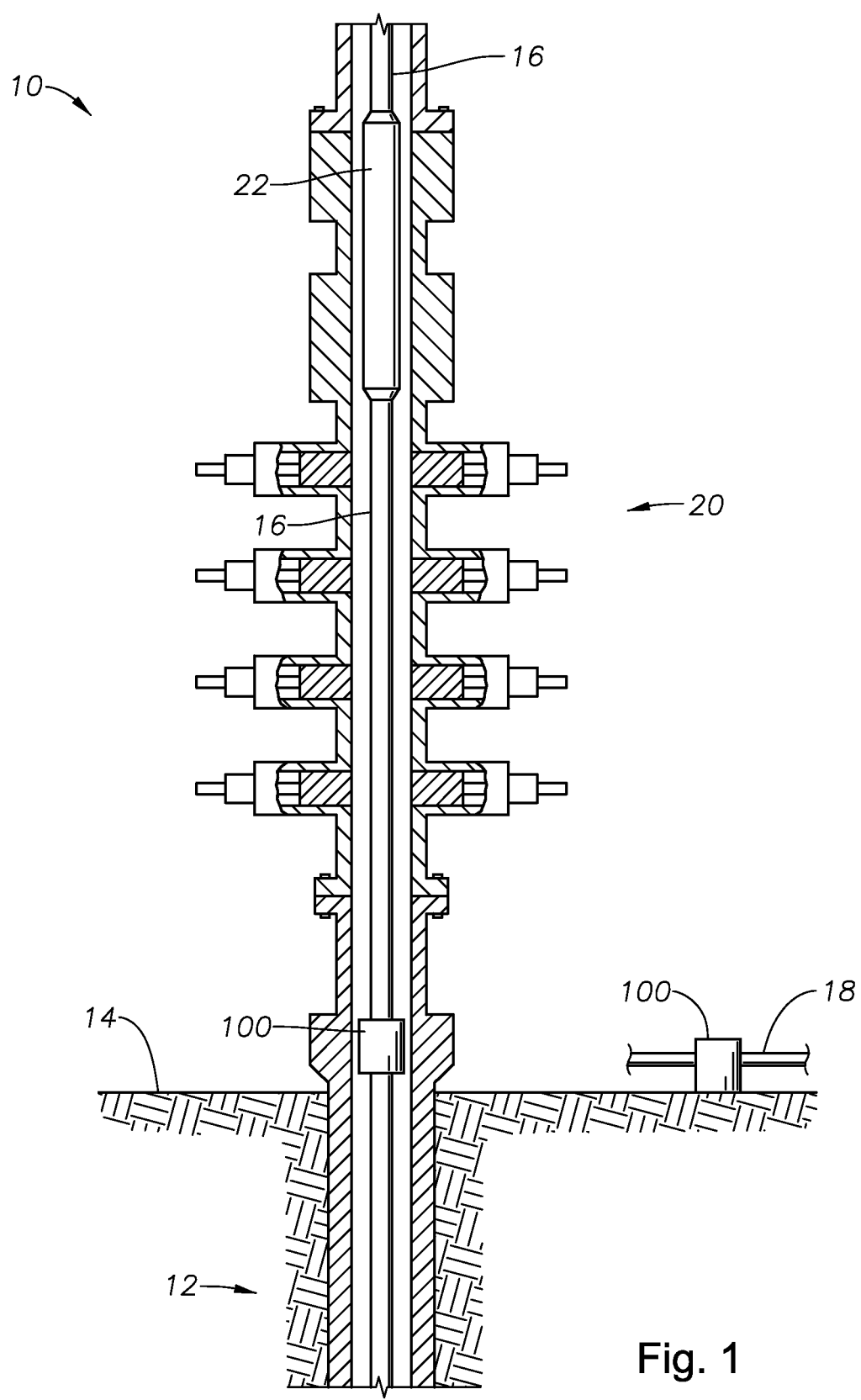
FIG. 1 is a schematic illustration of a well system having an ICE computing device positioned therein according to certain exemplary embodiments of the present invention.

Illustrative embodiments and related methodologies of the present invention are described below as they might be employed in an optical computing device utilizing one or more ICE structures to predict and mitigate the formation of hydrates in hydrocarbon environments. In the interest of clarity, not all features of an actual implementation or methodology are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments and related methodologies of the invention will become apparent from consideration of the following description and drawings.

Exemplary embodiments of the present invention are directed to an ICE computing device utilized to predict and/or mitigate the formation of hydrates along conduits comprising hydrocarbon fluid flow. As described herein, the present invention utilizes one or more ICE structures to monitor fluid flow through a conduit in real-time to determine the potential for hydrate formation. If the computations generated by the ICE computing device indicate that the measured fluid composition and operating parameters are adequate for hydrate formation, then one or more mitigation techniques may be employed. Such mitigation techniques may include, for example, manual or automatic injection of hydrate inhibiting chemicals into the conduit or adjustment of physical parameters to shift the hydrate envelope out of the active zone. Accordingly, hydrate formation may be predicted and mitigated to avoid costly remedial hydrate-related operations.

The exemplary ICE computing devices described herein utilize one or more ICE structures, also known as a Multivariate Optical Elements ("MOE"), to achieve the objectives of the present invention. An ICE computing device is a device configured to receive an input of electromagnetic radiation from a substance or sample of the substance and produce an output of electromagnetic radiation from a processing element. Fundamentally, ICE computing devices utilize ICE structures to perform calculations, as opposed to the hardwired circuits of conventional electronic processors. When electromagnetic radiation interacts with a substance, unique physical and chemical information about the substance is encoded in the electromagnetic radiation that is reflected from, transmitted through, or radiated from the sample. This information is often referred to as the substance's spectral "fingerprint." Thus, the ICE computing device, through use of the ICE structure, is capable of extracting the information of the spectral fingerprint of multiple characteristics/properties or analytes within a substance and converting that information into a detectable output regarding the overall properties of a sample. The design and operation of ICE structures are described in, for example, U.S. Pat. Nos. 6,198,531; 6,529,276; 7,697,141; and 8,049,881, each being owned by the Assignee of the present invention, Halliburton Energy Services, Inc., of Houston, Tex., the disclosure of each being hereby incorporated by reference in its entirety.

FIG. 1 illustrates two exemplary applications in which the present invention may be utilized. As illustrated in FIG. 1, one or more exemplary embodiments of ICE computing device 100 may be positioned at a variety of locations within a well system 10. An exemplary well system 10 comprises a wellbore 12 extending from a surface 14 of a hydrocarbon bearing formation, and may be cased or uncased. Although wellbore 12 is illustrated as vertical, it may also be deviated or horizontal. A subsea blow-out preventer ("BOP") 20 is positioned atop wellbore 12, while a subsea safety system 22 is coupled to a workstring 16 extending from the surface, as understood in the art.

As shown, in certain embodiments, ICE computing device 100 may be positioned along any conduit such as, for example, along workstring 16 and/or at surface 14 along a pipeline 18. Pipeline 18 may be a variety of pipes such as, for example, a processing or transportation pipeline, and may comprise fluid from one or more wells, etc. Moreover, workstring 16 may also be a variety of strings such as, for example, a production, testing, or injection string. Those ordinarily skilled in the art having the benefit of this disclosure will realize ICE computing device 100 may be utilized in a variety of applications, even non-oilfield related applications.

Figure 2:
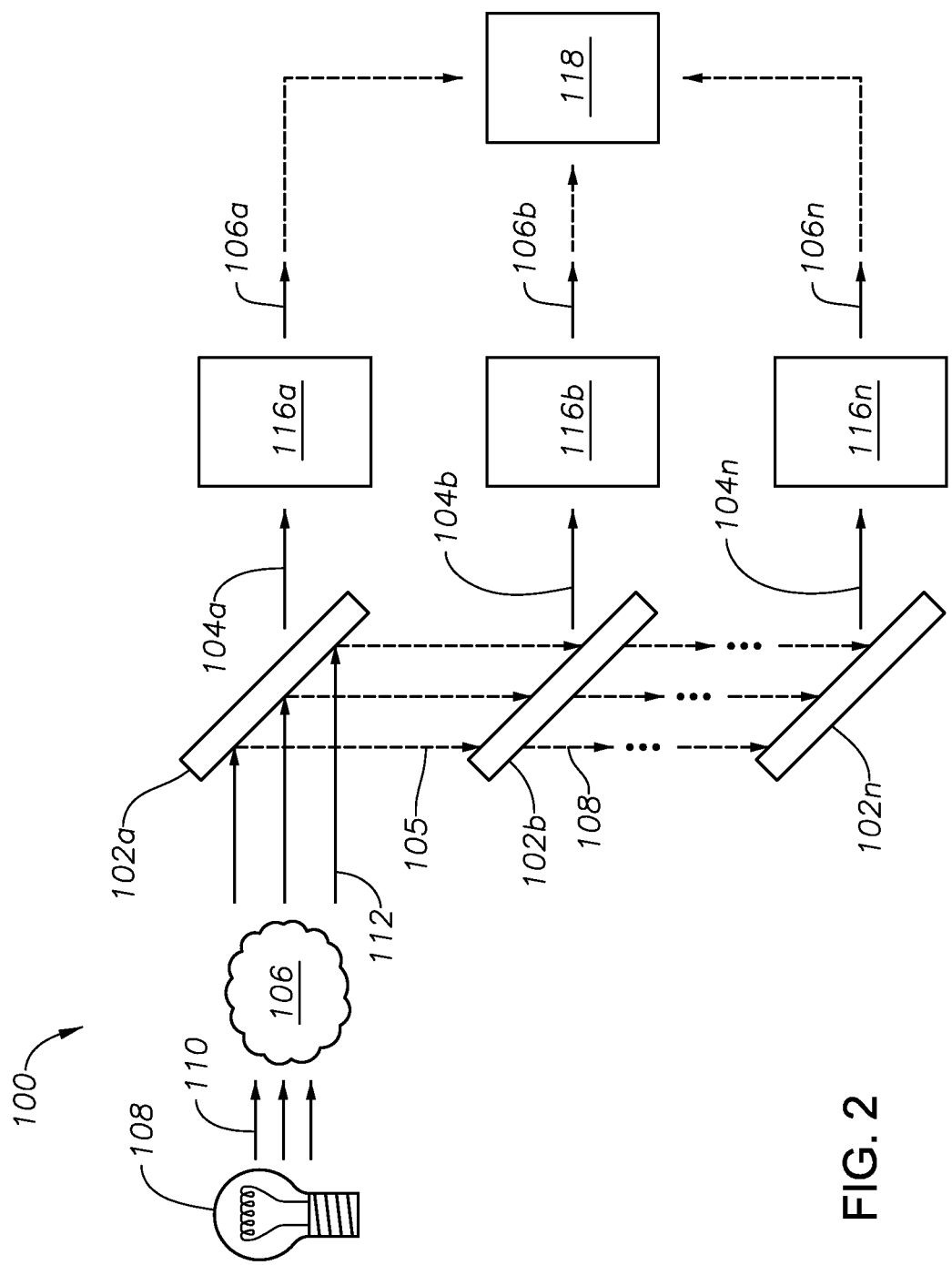
FIG. 2 is a block diagrammatical illustration of an ICE computing device utilized to predict and/or mitigate hydrate formation according to certain exemplary embodiments of the present invention.

FIG. 2 illustrates a block diagram of ICE computing device 100 according to certain exemplary embodiments of the present invention. As shown in FIG. 2, an electromagnetic radiation source 108 may be configured to emit or otherwise generate electromagnetic radiation 110. As understood in the art, electromagnetic radiation source 108 may be any device capable of emitting or generating electromagnetic radiation. For example, electromagnetic radiation source 108 may be a light bulb, light emitting device, laser, blackbody, photonic crystal, or X-Ray source, etc. In one embodiment, electromagnetic radiation 110 may be configured to optically interact with the sample 106 and generate sample-interacted light 112 directed to a first ICE 102.

While FIG. 2 shows electromagnetic radiation 110 as passing through the multiphase fluid sample 106 to produce sample-interacted light 112, it is also contemplated herein to reflect electromagnetic radiation 110 off of multiphase fluid sample 106, such as in the case of a multiphase fluid sample 106 that is translucent, opaque, or solid, and equally generate the sample-interacted light 112.

Sample 106 may be any fluid, solid substance or material such as, for example, rock formations, concrete, other solid surfaces, etc. In this specific embodiment, however, sample 106 is a multiphase fluid (comprising oil, gas, water, solids, for example) consisting of a variety of fluid properties such as, for example, C1-C4 and higher hydrocarbons, groupings of such elements, and saline water. Moreover, as defined herein, the term "property" means a chemical or physical characteristic or element contained in the multiphase fluid or which forms the multiphase fluid and which includes, but is not limited to SARA (saturates, asphaltene, resins, aromatics), solid particulate content such as dirt, mud, scale, sand, and similar contaminants, water, H2O ion-composition and content, saturation level, mass readings, hydrocarbon composition and content, gas composition and content, CO2, H2S and correlated PVT properties including GOR (gas-oil ratio), bubble point, density, a formation factor and viscosity among other properties. Furthermore, the term "property" as used herein includes calculated data and information, such as, for example, quantities, concentrations, relative proportions and fractions of measured elements and other properties, mass, volume, mass and volume flow rate, etc. of the multiphase fluid and its constituents. In addition, the properties may be measured indirectly, through measuring an indicator constituent (explained further below).

After being illuminated with electromagnetic radiation 110, multiphase fluid sample 106 containing an analyte of interest (a property of the sample, for example) produces an output of electromagnetic radiation (sample-interacted light 112, for example). Although not specifically shown, one or more spectral elements may be employed in ICE computing device 100 in order to restrict the optical wavelengths and/or bandwidths of the system and, thereby, eliminate unwanted electromagnetic radiation existing in wavelength regions that have no importance. As will be understood by those ordinarily skilled in the art having the benefit of this disclosure, such spectral elements can be located anywhere along the optical train, but are typically employed directly after the light source which provides the initial electromagnetic radiation. Various configurations and applications of spectral elements in optical computing devices may also be found in commonly owned U.S. Pat. Nos. 6,198,531; 6,529,276; and 8,049,881, as previously mentioned herein.

Still referring to the exemplary embodiment of FIG. 2, ICE computing device 100 includes first ICE 102a, second ICE 102b and additional ICE 102n, each configured to determine one property of multiphase fluid sample 106. In this embodiment, the properties determined include the presence and quantity of specific inorganic gases such as, for example, $CO_2$ and $H_2S$, organic gases such as methane (C1), ethane (C2) and propane (C3) and saline water. In certain embodiments, a single ICE may detect a single property, while in others a single ICE may determine multiple properties, as will be understood by those ordinarily skilled in the art having the benefit of this disclosure.

In the embodiment specifically depicted, the first ICE 102a is arranged to receive the sample-interacted light 112 from the sample 106. First ICE 102a is configured to transmit a first optically interacted light 104a to the first detector 116a and simultaneously convey reflected optically interacted light 105 toward the second ICE 102b. The second ICE 102b is configured to convey a second optically interacted light 104b via reflection toward the second detector 116b, and simultaneously transmit additional optically interacted light 108 toward the additional ICE 102n. The additional ICE 102n is configured to convey an additional optically interacted light 104n via reflection toward the additional detector 116n.

Those ordinarily skilled in the art having the benefit of this disclosure will readily recognize numerous alternative configurations of the first, second, and additional ICE 102a-n, without departing from the scope of the disclosure. For example, reflection of optically interacted light from a particular ICE may be replaced with transmission of optically interacted light, or alternatively configurations may include the use of mirrors or beam splitters configured to direct the electromagnetic radiation 110 (or sample-interacted light 112) to each of the first, second, and additional ICE 102a-n.

In certain exemplary embodiments, first, second, and additional detectors 116a-n may be configured to detect the first, second, and additional optically interacted light 104a-n, respectively, and thereby generate a first signal 106a, a second signal 106b, and one or more additional signals 106n, respectively. In some embodiments, the first, second, and additional signals 106a-n may be received by a local signal processor 118 communicably coupled to each detector 116a-n and configured to computationally combine the first, second, and additional signals 106a-n in order to determine the property of the multiphase fluid sample 106. Although illustrated as part of ICE computing device 100, signal processor 118 may be located remotely and, in such embodiments, signals 106a-n may be transmitted using wired or wireless methodologies, as understood in the art.

Accordingly, any number of ICE may be arranged or otherwise used in series in order to determine the desired property of the multiphase fluid sample 106 that can be used to determine if conditions exists to form hydrates. In some embodiments, each of the first, second, and additional ICE 102a-n may be specially-designed to detect the particular property of interest or otherwise be configured to be associated therewith. In other embodiments, however, one or more of the first, second, and additional ICE 102a-n may be configured to be disassociated with the particular property of interest, and/or otherwise may be associated with an entirely different property of the multiphase fluid sample 106. In yet other embodiments, each of the first, second, and additional ICE 102a-n may be configured to be disassociated with the particular property of interest, and otherwise may be associated with an entirely different property of the multiphase fluid sample 106. Moreover, although not shown, ICE computing device 100 also comprises the necessary components to produce the pressure and temperature measurements, or operating conditions, associated with multiphase fluid sample 106 necessary to determine operating conditions, as will be understood by those ordinarily skilled in the art having the benefit of this disclosure.

Accordingly, through use of exemplary embodiments of ICE computing 100, the amount and composition of the gas phase and water phase of multiphase fluid sample 106 may be constantly monitored for properties and operating conditions adequate to form hydrates. Once signals 106a-n are output by detectors 116a-n, signals 106a-n may then be processed by signal processor 118 to define the hydrate envelope for the particular measured set of operating conditions. As understood in the art, the hydrate envelope is the range of operating conditions (pressure, temperatures, gas composition, etc.) under which hydrates can form. To calculate the hydrate envelope, there are a variety of software platforms which may be embodied within and executed by signal processor 118 such as, for example, PVTSim™ or similar platforms, as will be understood by those ordinarily skilled in the art having the benefit of this disclosure.

Once signal processor 118 defines the hydrate envelope, it then determines whether the Equation of State ("EOS") computations indicate that the measured properties of multiphase fluid sample 106 (i.e., signals 106a-n) and associated operating parameters (compositions, pressures and temperature measurements, for example) are adequate for hydrate formation. If the determination is yes, signal processor 118 may output a signal (alert signal, for example) indicating that corrective action is necessary. Such corrective action may include, for example, manual or automatic injection of hydrate inhibiting chemicals or adjusting physical parameters such as, for example, temperature and pressure, to shift the hydrate envelope out of the active zone.

In certain other exemplary embodiments, ICE computing device 100 may continuously monitor changing downhole conditions to determine trends. In such embodiments, even though a specific set of readings does not indicate a potential for hydrate formation, if a trend implies that anticipated changes could lead to hydrate formation, signal processor 118 may output a signal to initiate correction action before hydrate formation becomes an issue.

Figure 3:
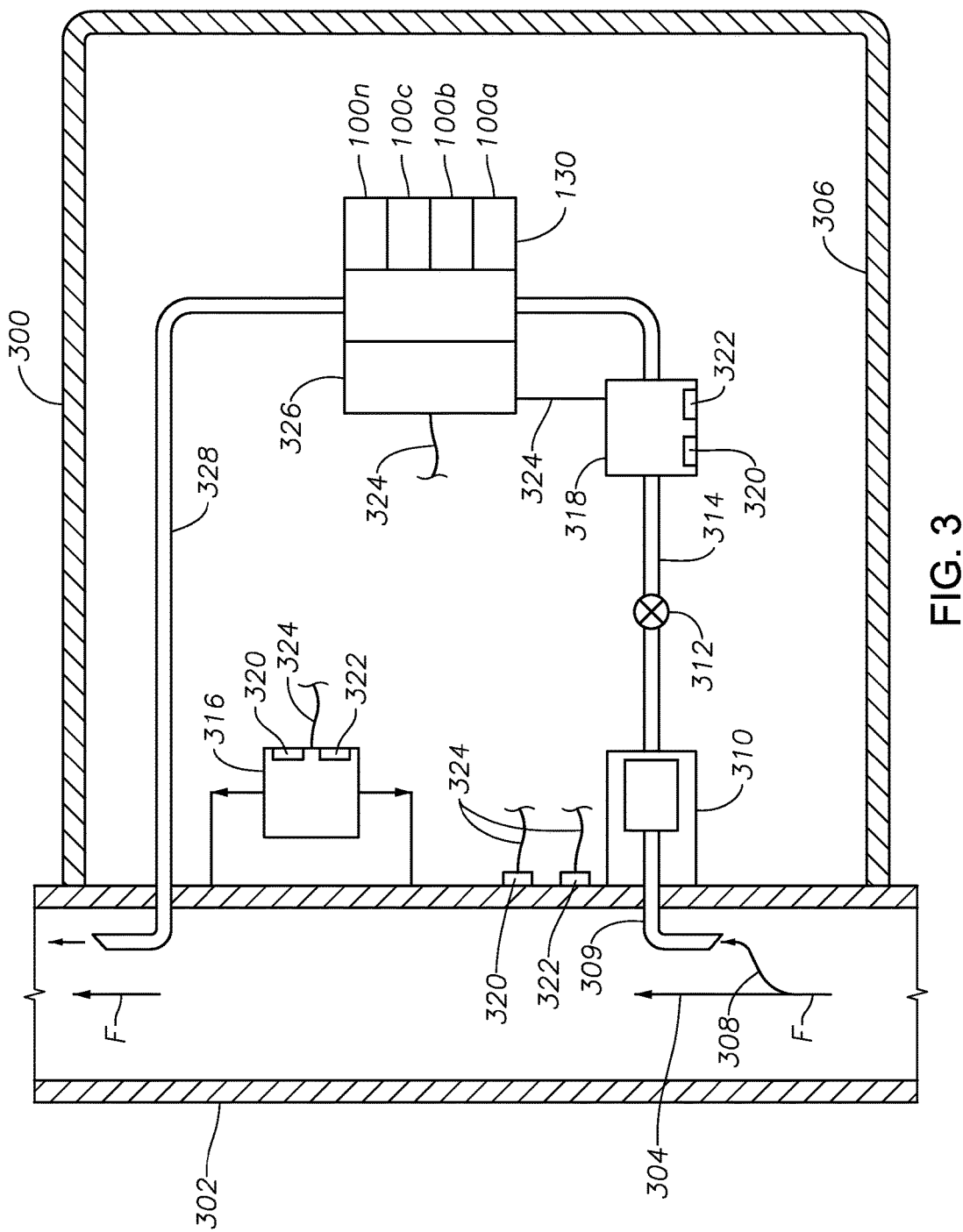
FIG. 3 is a block diagrammatical illustration of the fluid flow through an ICE computing device according to certain exemplary embodiments of the present invention.

FIG. 3 is a schematic view of an exemplary flow diagram for analyzing multiphase fluid flow using ICE computing device 100, according to one or more exemplary embodiments of the present invention. An exemplary hydrate prediction and mitigation module 300 has been attached to a primary conduit (tubular, for example) 302 through which a primary stream 304 of multiphase fluid F is flowing. Hydrate prediction and mitigation module 300 comprises a housing 306 which may be, for example, a stainless steel, temperature and pressure resistant body. In addition, housing 306 may be magnetic so that it is readily attached and detached from the primary conduit 302. However, those ordinarily skilled in the art having the benefit of this disclosure realize housing 306 may be attached in a variety of other ways.

To analyze the multiphase fluid F, a sample multiphase fluid stream 308 is extracted from the primary stream 304 and subjected to at least one ICE computing device 100 via an inflow conduit 309. In this exemplary embodiment, ICE computing device 100 comprises a plurality of computing devices 100a, 100b, 100c, 100n. Collection of the sample stream 308 is performed by a sample collection assembly 310 such as, for example, a static probe, impulse actuated sampler, flow-controlled or time-controlled sampler, impeller type samplers, permanent or removable probes, etc. Nevertheless, sample collection assembly 310 provides a continuous flow of a sample stream across the ICE computing device 100 for continuous analysis (Understandable, the sample fluid flow may be stopped when readings are not desired.). In other embodiments, a vortex mixer and a travelling probe, such as those used during iso-kinetic sampling, may also be utilized. Accordingly, those ordinarily skilled in the art having the benefit of this disclosure realize there are a variety of sample collection assemblies with may be utilized. Hydrate prediction and mitigation module 300 may also include control valves, such as valve 312, for controlling fluid flow through the various conduits, such as conduit 314.

Furthermore, in certain exemplary embodiments, hydrate prediction and mitigation module 300 will employ various other fluid property measuring devices, such as a differential pressure fluid meter 316, fluid flow rate (volumetric and/or mass) meter 318, and various pressure sensors 320 and temperature sensors 322, etc. In certain embodiments, these meters and sensors will be utilized to determine the pressures and temperatures of primary stream 304 inside primary conduit 302, as this is where hydrate formation is most likely to occur. However, it is also envisioned that such readings may also be taken of sample multiphase fluid stream 308. Nevertheless, hydrate prediction and mitigation module 300 also includes a plurality of communication devices for transmitting data, such as wiring 324, wireless devices, etc., as are known in the art. The various data from the sensors, valves, flow meters, and ICE computing devices 100a-n are transmitted to a processor 326. In certain embodiments, processor 326 and ICE computing devices 100a-n are located a single housing 130, while in other embodiments processor 326 is located remotely from the remainder of ICE computing devices 100a-n.

Hydrate prediction and mitigation module 300 may also include a return conduit 328 for returning sample multiphase fluid stream 308 to primary stream 304. In other embodiments, however, sample multiphase fluid stream 308 may be otherwise disposed of. Moreover, although not shown, hydrate prediction and mitigation module 300 can include fluid flow equipment as known in the art, such as, for example, a pump, compressors, turbulence generators, holding tanks and various valving, such as one-way valves, manual valves, emergency shut-off valves, etc.

Still referring to the exemplary embodiment illustrated in FIG. 3, each ICE computing device 100a-n detects and quantifies a target constituent, or property, of the multiphase fluid flow F in the sample multiphase fluid stream 308. As described previously, the properties to be detected can be the presence and quantities of constituents of sample multiphase fluid stream 308, such as, for example, organic C1-C3 gases, as well as organic liquids, such as, for example, water phases and saturation. In addition, pressure sensors 320 and temperature sensors 322 are utilized to detect the operating conditions existing within primary conduit 302. Thereafter, as previously described, the data related to multiphase fluid properties and the operating conditions are then transmitted to processor 326, which defines the hydrate envelope accordingly to determine whether the properties and conditions within primary conduit 302 are adequate to form hydrates. If such conditions exist, alert signals and/or mitigation operations may be transmitted and conducted accordingly.

The exemplary embodiments described herein provide a number of advantages. For example, the present invention provides a minimally intrusive device and method allowing continuous monitoring of the environment and gas composition, so that a real-time understanding of the potential for hydrate formation is realized. In addition, such an efficient and real-time understanding of the fluids and environmental conditions allows for the application of appropriate mitigation techniques, thus providing considerable commercial and competitive advantages.

An exemplary methodology of the present invention provides an optical computing method to predict hydrate formation, the method comprising allowing fluid to flow through a first conduit; separating a sample fluid from the fluid flowing through the first conduit; allowing the sample fluid to flow through a second conduit; detecting at least one property of the sample fluid corresponding to hydrate formation using at least one ICE computing device positioned along the second tubular; and determining whether the detected at least one property is adequate for hydrate formation. In another method, the at least one property of the sample fluid comprises at least one of a C1 hydrocarbon, C2 hydrocarbon, C3 hydrocarbon, C4 hydrocarbon or water. In another, the at least one property of the sample fluid further comprises at least one of a pressure within the first conduit or a temperature of the first conduit.

Yet another method further comprises generating an alert signal when it is determined the detected at least one property is adequate for hydrate formation. Another further comprises performing at least one mitigation technique when it is determined the detected at least one property is adequate for hydrate formation. In yet another, the first tubular is part of a pipeline or wellbore tubular.

An exemplary embodiment of the present invention provides an optical computing device to predict hydrate formation comprising an electromagnetic radiation source that optically interacts with a sample fluid to produce sample-interacted light; an ICE that optically interacts with the sample-interacted light to generate optically interacted light that corresponds to at least one property of the sample fluid relating to hydrate formation; and a detector positioned to receive the optically interacted light and thereby generate a signal corresponding to the at least one property relating to hydrate formation, the signal being utilized to determine whether the at least one property is adequate for hydrate formation. In another, the device further comprises a signal processor communicably coupled to the detector to determine whether the at least one property is adequate for hydrate formation. In another, at least one property of the sample fluid comprises at least one of a C1 hydrocarbon, C2 hydrocarbon, C3 hydrocarbon, C4 hydrocarbon or water.

In another, the at least one property of the sample fluid further comprises at least one of a pressure within the first conduit or a temperature of the first conduit. In yet another, the signal processor is configured to generate an alert signal when it is determined the at least one property is adequate for hydrate formation. In another, the optical computing device is positioned along a primary conduit, the optical computing device further comprising an inflow conduit extending into the primary conduit to separate the fluid sample from a primary fluid stream and communicate the fluid sample to the ICE; and a return conduit to return the fluid sample back to the primary conduit. In yet another, the primary conduit is a pipeline or wellbore tubular.

Yet another exemplary methodology of the present invention provides an optical computing method to predict hydrate formation, the method comprising receiving a sample fluid into an ICE computing device; detecting at least one property of the sample fluid corresponding to hydrate formation using the ICE computing device; and determining whether the detected at least one property is adequate for hydrate formation. In another, the at least one property of the sample fluid comprises at least one of a C1 hydrocarbon, C2 hydrocarbon, C3 hydrocarbon, C4 hydrocarbon or water. In yet another, the at least one property of the sample fluid further comprises at least one of a pressure or temperature reading. In another, the method further comprises generating an alert signal when it is determined the detected at least one property is adequate for hydrate formation.

Another further comprises performing at least one mitigation technique when it is determined the detected at least one property is adequate for hydrate formation. In yet another, the ICE computing device is positioned along a pipeline or wellbore tubular. In another, determining whether the detected at least one property is adequate for hydrate formation further comprises continuously monitoring the detected at least one property; determining one or more trends based upon the detected at least one property; and utilizing the one or more trends to determine whether hydrate formation will occur.

Although various embodiments and methodologies have been shown and described, the invention is not limited to such embodiments and methodologies and will be understood to include all modifications and variations as would be apparent to one skilled in the art. Therefore, it should be understood that the invention is not intended to be limited to the particular forms disclosed. Rather, the intention is to cover all modifications, equivalents and alternatives falling within the spirit and scope of the invention as defined by the appended claims.

What is claimed is:

1. An optical computing method to predict hydrate formation, the method comprising:
   allowing fluid to flow through a first conduit;
   separating a sample fluid from the fluid flowing through the first conduit;
   allowing the sample fluid to flow through a second conduit;
   detecting at least one property of the sample fluid corresponding to hydrate formation using at least one Integrated Computational Element ("ICE") computing device positioned along the second conduit;
   determining whether the detected at least one property is adequate for hydrate formation; and
   performing at least one mitigation technique when it is determined that the detected at least one property is adequate for hydrate formation.

2. A method as defined in claim 1, wherein the at least one property of the sample fluid comprises at least one of a C1 hydrocarbon, C2 hydrocarbon, C3 hydrocarbon, C4 hydrocarbon or water.

3. A method as defined in claim 2, wherein the at least one property of the sample fluid further comprises at least one of a pressure within the first conduit or a temperature of the first conduit.

4. A method as defined in claim 1, further comprising generating an alert signal when it is determined the detected at least one property is adequate for hydrate formation.

5. A method as defined in claim 1, wherein performing the at least one mitigation technique includes at least one of adjusting physical parameters of the fluid or injecting hydrate inhibiting chemicals into the first conduit when it is determined the detected at least one property is adequate for hydrate formation.

6. A method as defined in claim 1, wherein the first conduit is part of a pipeline or wellbore tubular.

7. An optical computing device to predict hydrate formation, comprising:
   an electromagnetic radiation source that optically interacts with a sample fluid to produce sample-interacted light;
   an Integrated Computational Element ("ICE") that optically interacts with the sample-interacted light to generate optically interacted light that corresponds to at least one property of the sample fluid relating to hydrate formation; and
   a detector positioned to receive the optically interacted light and thereby generate a signal corresponding to the at least one property relating to hydrate formation, the signal being utilized to determine whether the at least one property is adequate for hydrate formation.

8. An optical computing device as defined in claim 7, further comprising a signal processor communicably coupled to the detector to determine whether the at least one property is adequate for hydrate formation.

9. An optical computing device as defined in claim 7, wherein the at least one property of the sample fluid comprises at least one of a C1 hydrocarbon, C2 hydrocarbon, C3 hydrocarbon, C4 hydrocarbon or water.

10. An optical computing device as defined in claim 9, wherein the at least one property of the sample fluid further comprises at least one of a pressure within the first conduit or a temperature of the first conduit.

11. An optical computing device as defined in claim 8, wherein the signal processor is configured to generate an alert signal when it is determined the at least one property is adequate for hydrate formation.

12. An optical computing device as defined in claim 7, wherein the optical computing device is positioned along a primary conduit, the optical computing device further comprising:
   an inflow conduit extending into the primary conduit to separate the fluid sample from a primary fluid stream and communicate the fluid sample to the ICE; and
   a return conduit to return the fluid sample back to the primary conduit.

13. An optical computing device as defined in claim 12, wherein the primary conduit is a pipeline or wellbore tubular.

14. An optical computing method to predict hydrate formation, the method comprising:
   receiving a sample fluid into an Integrated Computational Element ("ICE") computing device;
   detecting at least one property of the sample fluid corresponding to hydrate formation using the ICE computing device;
   determining whether the detected at least one property is adequate for hydrate formation; and
   performing at least one mitigation technique when it is determined the detected at least one property is adequate for hydrate formation.

15. A method as defined in claim 14, wherein the at least one property of the sample fluid comprises at least one of a C1 hydrocarbon, C2 hydrocarbon, C3 hydrocarbon, C4 hydrocarbon or water.

16. A method as defined in claim 15, wherein the at least one property of the sample fluid further comprises at least one of a pressure or temperature reading.

17. A method as defined in claim 14, further comprising generating an alert signal when it is determined the detected at least one property is adequate for hydrate formation.

18. A method as defined in claim 14, wherein performing the at least one mitigation technique includes at least one of adjusting physical parameters of the fluid or injecting hydrate inhibiting chemicals into the first conduit when it is determined the detected at least one property is adequate for hydrate formation.

19. A method as defined in claim 14, wherein the ICE computing device is positioned along a pipeline or wellbore tubular.

20. A method as defined in claim 14, wherein determining whether the detected at least one property is adequate for hydrate formation further comprises:
   continuously monitoring the detected at least one property;
   determining one or more trends based upon the detected at least one property; and
   utilizing the one or more trends to determine whether hydrate formation will occur.

* * * * *